United States Patent
Shapiro et al.

[11] Patent Number: 6,155,098
[45] Date of Patent: *Dec. 5, 2000

[54] DEWPOINT SENSOR

[75] Inventors: Andrew Philip Shapiro, Niskayuna; Anthony John Dean, Scotia, both of N.Y.

[73] Assignee: General Electric Company, Schenectady, N.Y.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/415,715

[22] Filed: Oct. 12, 1999

Related U.S. Application Data

[63] Continuation of application No. 09/191,248, Nov. 13, 1998.
[51] Int. Cl.[7] .................................................. G01N 25/66
[52] U.S. Cl. ......................... 73/29.01; 73/29.05; 374/16; 374/22
[58] Field of Search ............................... 73/29.01, 29.03, 73/29.05; 374/16, 22

[56] References Cited

FOREIGN PATENT DOCUMENTS 1301477  5/1992  Canada ................................ 374/22

OTHER PUBLICATIONS

Inamatsu et al., "Dew–Point Hygrometer by Quartz Crystal", Moisture, Humidity, Process International Symposium, 1985, pp. 379–388.

*Primary Examiner*—Daniel S. Larkin
*Attorney, Agent, or Firm*—Patrick K. Patnode; Marvin Snyder

[57] ABSTRACT

A dewpoint sensor comprises a pressure vessel having an entry port, an exit port, and a temperature controlled plate. A quartz crystal resonator is housed within the pressure vessel and disposed in intimate contact with the temperature controlled plate. A temperature sensor is disposed to generate signals representative of the quartz crystal resonator temperature. Circuitry is coupled to the quartz crystal resonator and the temperature sensor, which circuitry is configured to control the temperature of the quartz crystal resonator, to measure the frequency of the quartz crystal resonator and to monitor the temperature signals and the frequency of the quartz crystal resonator when exposed to a flow between the entry port and the exit port so as to calculate a dewpoint value of the flow.

1 Claim, 6 Drawing Sheets

DEWPOINT SENSOR

This application is a continuation of application Ser. No. 09/191,248, filed Nov. 13, 1998, which is hereby incorporated by reference in its entirety.

BACKGROUND OF THE INVENTION

This invention relates generally to dewpoint sensors and more specifically to non-optical dewpoint sensors.

Industrial power generation gas turbine engines include a compressor for compressing air that is mixed with fuel and ignited in a combustor for generating combustion gases. The combustion gases flow to a turbine that extracts energy for driving a shaft to power the compressor and produces output power for powering an electrical generator, for example. The turbine is typically operated for extended periods of time at a relatively high base load for powering the generator to produce electrical power to a utility grid, for example. Exhaust emissions from the combustion gases are therefore a concern and are subjected to mandated limits.

Low emission combustion systems are designed to produce low emissions and high combustion efficiency while burning natural gas fuel that is assumed to be free of liquid or solid contaminants. In fact, pipeline gas is at times contaminated with condensed liquid hydrocarbons (to varying degrees) as well as other solid particulate contaminants. It is highly desirable to minimize the effects of these contaminants on gas turbine combustor performance, either by their removal or by robust combustor design. As low emission systems have become more prevalent in the field and exposed to a variety of natural gas sources while performing with lower and lower emission goals, the presence of varying amounts of liquid hydrocarbons in the fuel source has become an increasing operational issue.

The quality of natural gas supplied to gas turbines is an important variable in turbine performance. The principle component of natural gas is methane, which typically accounts for over 90% of the mass. Other components in natural gas may include heavier hydrocarbons, oils and water. In gas turbines equipped with combustors that premix fuel and air prior to ignition, the chemical composition of the gas is particularly important because of the potential for ignition to occur within the mixing zone. The effect of heavier hydrocarbons and oils in the gas stream is to lower the autoignition temperature of the mixture. Natural gas with high concentrations of these species is more likely to ignite in the mixing zone of the combustors than in an intended flame holder region.

Certain optical dewpoint meters can determine the dewpoint of either water or hydrocarbons in natural gas. One instrument uses two chilled surfaces, each with different surface properties to distinguish between the water and hydrocarbon dewpoint. A second unit uses a specially shaped mirror that is designed to detect hydrocarbon dewpoint. To measure water dewpoint, this unit employs a second ceramic sensor that measures impedance. Both instruments are rendered inoperable when the optical surface is contaminated by certain compounds such as glycols, lubricating oils and hydrocarbons.

Non-optical instruments exist for the measurement of water dewpoint. One unit includes humidity sensors based on electrical resistivity changes of a hygroscopic polymer coating on a ceramic substrate and sensors based on the electrical capacitance changes of a thin layer of polymer between two metal electrodes. While these polymer-based sensors do not rely on optically clean surfaces, they are only useful to measure water dewpoints, and could not be used to measure hydrocarbon dewpoints.

Quartz crystal resonators (QCR) have been used to measure water humidity and dewpoint in air and other gases. Canadian patent 1,301,477 (1992) by Claude Porltier et al. describes a QCR system to measure humidity of gases. Teruko Inamatsu and Chiharu Takahashi (1985) describe a dewpoint hygrometer based on QCR for humidity measurements. These patents, however, do not address applications to other condensable gases such as organic vapors and natural gas.

D. McKeown et al. (1985) describe the use of thermally controlled QCRs for monitoring surface contamination on the NASA Spacelab I. In this reference, non-aqueous volatile condensable material is detected under near-vacuum (low Earth orbit) conditions. Organic materials such as plasticizers and rocket exhaust products are presumed to be the source of the contamination. This system does not operate at high pressures or have a controlled amount of sweep gas pass the sensor. Nor is this device designed to determine the dewpoint of the surrounding atmosphere.

In none of the known art of using (QCRs) for dewpoint measurement has a method been described to determine the dewpoint without actually causing condensation to occur on the crystal. Such condensation can lead to fouling of the crystal by providing sites for particulates to stick to. These particulates may not be removable during the temperature cycling of the crystal.

Accordingly, there is a need in the art for an improved non-optical dewpoint sensor.

SUMMARY OF THE INVENTION

A dewpoint sensor comprises a pressure vessel having an entry port, an exit port, and a temperature controlled plate. A quartz crystal resonator is housed within the pressure vessel and is disposed in intimate contact with the temperature controlled plate. A temperature sensor is disposed to generate signals representative of the quartz crystal resonator temperature. Circuitry is coupled to the quartz crystal resonator and the temperature sensor, which circuitry is configured to control the temperature of the quartz crystal resonator, to measure the frequency of the quartz crystal resonator and to monitor the frequency of the quartz crystal resonator when exposed to a flow between the entry port and the exit port so as to calculate a dewpoint temperature value of the flow.

DETAILED DESCRIPTION OF THE INVENTION

Figure 1:
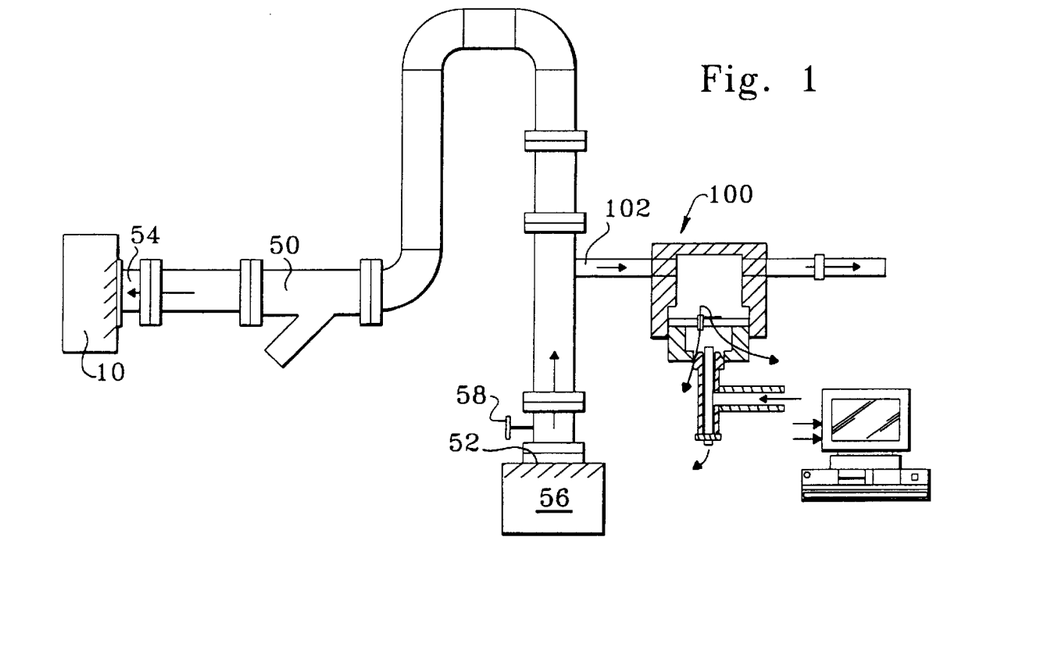
FIG. 1 is schematic, cross-sectional side elevation view of a pipeline and a dewpoint sensor in accordance with one embodiment of the instant invention.

A pipeline 50 comprising an inlet 52 and an outlet 54 provides fluid communication between a fuel source 56 and a fuel consumer 10, for example, a power turbine, as shown in FIG. 1. A shut off valve 58 is disposed within pipeline 50, which valve 58 is movable between a fully open position and a fully closed position to allow or prevent fuel flow, respectively, from fuel source 56 to power turbine 10.

As discussed above, detecting that a proper fuel quality is present, prior to combustion within power turbine 10 is becoming increasingly important.

In accordance with one embodiment of the instant invention, a dewpoint sensor 100 is coupled to pipeline 50. Typically, a conduit 102 or the like provides flow communication between pipeline 50 and dewpoint sensor 100.

Figure 2:
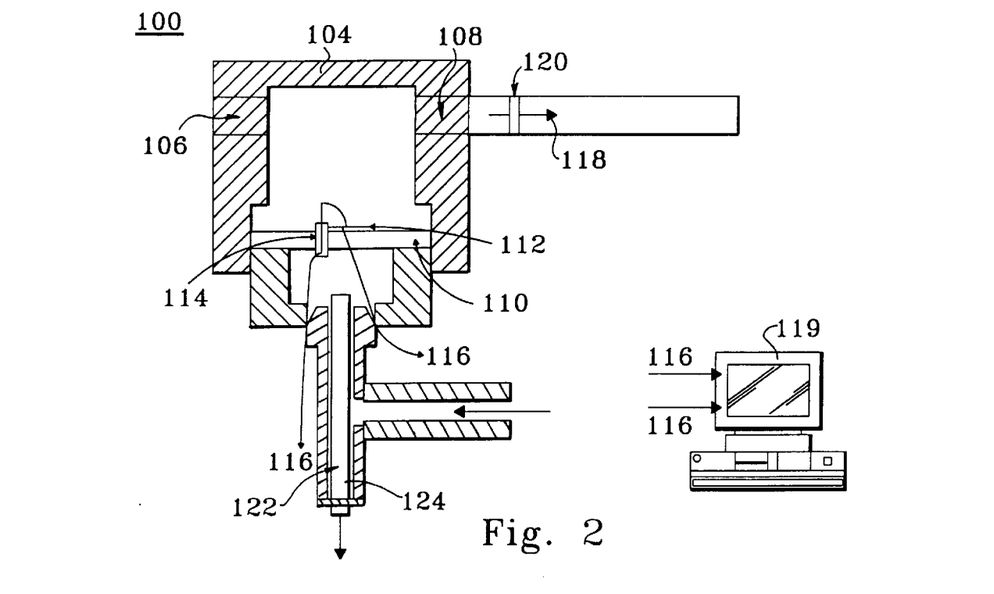
FIG. 2 is an enlarged schematic cross-sectional side elevation view of a dewpoint sensor in accordance with one embodiment of the instant invention.

Dewpoint sensor 100 comprises a pressure vessel 104 having an entry port 106, an exit port 108 and a temperature controlled plate 110, as best shown in FIG. 2. A quartz crystal resonator 112 is housed within pressure vessel 104 and is disposed in intimate contact with temperature controlled plate 110. A temperature sensor 114 is disposed to generate signals representative of the temperature of quartz crystal resonator 112. Temperature sensor 114 typically comprises a thermistor, a thermocouple or the like.

Circuitry 116 is coupled to quartz crystal resonator 112 and temperature sensor 114. Circuitry 116 is configured to control the temperature of quartz crystal resonator 112, to measure the frequency of quartz crystal resonator 112, and to monitor the temperature signals and the frequency of quartz crystal resonator 112 when exposed to a fuel flow 118 between entry port 106 and exit port 108 so as to calculate a dewpoint value of fuel flow 118 in a manner discussed in greater detail below.

In one embodiment, circuitry 116 includes a power input and a processor for monitoring the signals and generating an output signal. In another embodiment, circuitry 116 comprises a computer 119 for processing signals and generating a dewpoint report and display.

Typically, fuel flow 118 comprises a natural gas, for example, propane, hexane, heptane, gas derived from coal, methane or the like. As discussed above, fuel flow 118 flows from fuel source 56 to power turbine 10. A slipstream of fuel flow 118 is directed from pipeline 50 through conduit 102 into entry port 106 of pressure vessel 104.

While the instant invention is shown connected to a pipeline 50 for turbine engine 10, this device could also be applied to monitor the quality of process gases, not necessarily intended for combustion, in which the composition can be determined by measurement of dewpoint. Examples of such gas mixtures are water ammonia mixtures used in refrigeration cycles and feed stocks for the synthesis of polymer materials. Additionally, the instant invention can be utilized for: monitoring gas quality at the exit of a cryogenic gas processing system; monitoring gas quality at the custody transfer point between a gas producer and a gas transmission company; monitoring gas quality at the custody transfer point between a gas transmission company and a local distribution company; monitoring gas quality at a compressor station used to compress gas for natural gas powered vehicles, or the like.

A back pressure valve 120 is typically disposed at exit port 108 to control the flow through pressure vessel 104. In one embodiment, back pressure valve 120 maintains the pressure of pressure vessel 104 substantially equal to the pressure of pipeline 50 (FIG. 1).

Temperature controlled plate 110 is typically disposed in thermal intimacy with a cooling device 122 or a heating device 124. Cooling device 122 may comprise a vortex tube cooler, a Peltier device or the like. A vortex tube cooler uses compressed air as an energy source. As the air is expanded in the vortex tube, the air is separated into two streams, one hotter and one cooler than the supply air. By generating a hotter air stream it is possible to cool the cooler stream much more than can be achieved by expanding the supply air in a conventional manner. A Peltier device employs the thermal electric properties of dissimilar materials, usually metals or semiconductors configured as electrodes in an electric circuit. By applying an external voltage to the Peltier device one electrode becomes hotter and one will become cooler than the ambient conditions. Heating device 124 may comprise an electric heater, a high temperature stream of a vortex cooler, or a Peltier device operated with opposite voltage polarity from the cooling mode, or the like.

Temperature controlled plate 110 is typically made of material having a high thermal conductivity value like copper or the like. Control plate 110 may be plated with a corrosion inhibiting metal, such as gold, to prevent reaction with components of natural gas.

Electrodes contacting each side of QCR 112, but not inhibiting the oscillating motion, are fed out to circuitry 116 to measure the resonant frequency of the crystal. Temperature sensor 114 generates signals that correspond to the temperature of the crystal. By monitoring temperature and frequency change as the crystal is cooled, the dewpoint can be determined.

Because crystals are sensitive to nanograms per square centimeter deviation in adsorbed mass, the abrupt frequency changes that will occur when liquids condense on the surface will provide a robust indication of a condensation event.

A significant advantage of the device is that it detects changes in frequencies, so that if contamination accumulates on the crystal, which contamination is not desorbed during temperature cycling of the device, the initial frequency at a given starting temperature may change with time, however, the temperature at which an abrupt frequency change occurs is not affected. Additionally, dewpoint sensor 100 measures the dewpoint whether the condensate is water or an organic material.

Figure 3:
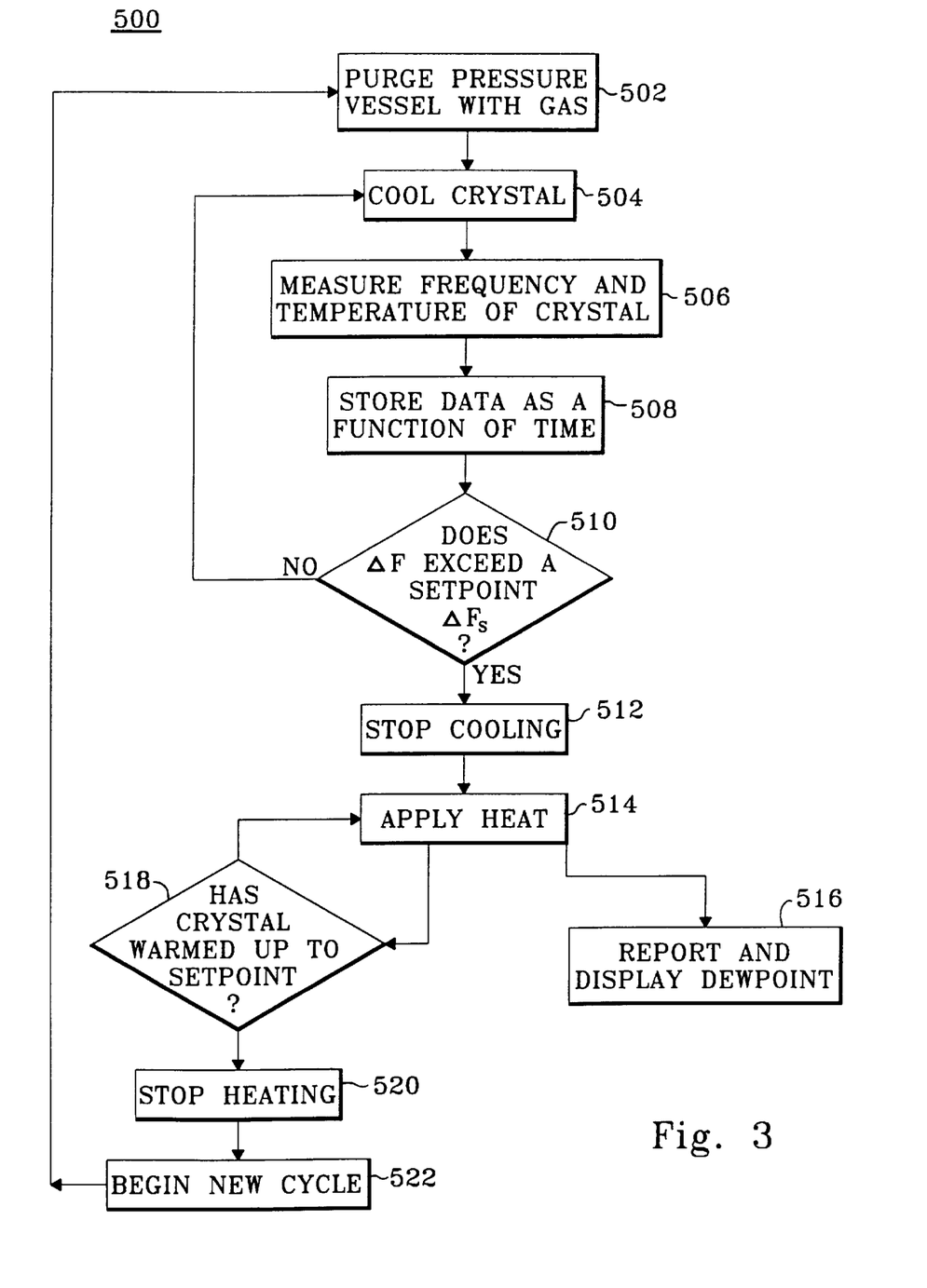
FIG. 3 is a flow chart depicting method steps in accordance with one embodiment of the instant invention.

A method for determining gas quality using dewpoint sensor 100 is depicted in flow chart 500 of FIG. 3. A control structure is inputted into circuitry 116, for example, by programming into memory of an application specific integrated circuit (ASIC) or is embedded in the form of algorithms in one or more computers 119 such as a work station. Other types of computers can be used, however, such as a minicomputer, a microcomputer, or a supercomputer, for example. The programming or algorithm performed may be programmed in C, C++, JAVA, Basic, MATLAB, FORTRAN, or other programming languages.

First, as shown in block 502, pressure vessel 104 (FIG. 2) is purged with a slipstream of gas flow 118. At block 504 (FIG. 3), circuitry 116 (FIG. 2) generates a signal to cooling device 122 to begin cooling QCR 112. Next, at block 506 (FIG. 3) circuitry 116 (FIG. 2) measures the frequency and temperature of QCR 112.

At block 510, circuitry 116 (FIG. 2) monitors the frequency of QCR 112 to determine if the change in frequency ($\Delta F$) over a predetermined period of time is greater than a set point change in frequency ($\Delta Fs$). In this embodiment, $\Delta F$ is selected to coincide with the dewpoint temperature of the flow. If the value of ΔF does not exceed the value of ΔFs, the control sequence returns to block 504 (FIG. 3) and continues cooling QCR 112 (FIG. 2).

If, however, the value of ΔF exceeds the value of ΔFs, the temperature of QCR 112 has substantially reached the dewpoint temperature of the gas flow and the dewpoint temperature is known. At block 516 (FIG. 3), the dewpoint temperature is reported, stored in a data base, or displayed to a system user. At block 512, the cooling is stopped. Heat is then applied to the crystal at block 514.

At block 518, circuitry 116 (FIG. 2) monitors the temperature of the crystal to determine if the crystal has warmed up to a setpoint temperature. If the temperature of the crystal does not exceed the setpoint temperature, the control sequence returns to block 514 (FIG. 3) and more heat is applied to the crystal.

If, however, the temperature of the crystal exceeds the setpoint temperature, the control sequence advances to block 520.

At block 520, circuitry 116 generates a signal to heating device 124 (FIG. 2) to stop heating. At block 522, the control sequence begins a new cycle and returns to block 502.

If the dewpoint temperature is above a setpoint indicating contamination, circuitry 116 may initiate a system control, for example, limit turbine engine 10 to low load operation. Additionally, if the dewpoint temperature rises above a setpoint temperature, circuitry 116 may initiate an algorithm to look at combustion system anomalies, or, for example, sound an alarm or otherwise alert a system user.

In one embodiment of the instant invention, the dewpoint of the flow may be determined without cooling the crystal to the dewpoint temperature. This prevents accumulation of liquids and particulates which may foul the crystal over time.

In order to determine the dewpoint, the crystal temperature and frequency data are collected and analyzed using a well-studied model for physisorption of vapor molecules on solid surfaces. This Brunauer-Emmett-Teller (B.E.T.) equilibrium theory can be expressed as $$\theta = x\left\{\frac{c-1}{1+x(c-1)} + \frac{1}{1-x}\right\} \quad \text{Eq. 1)}$$

where θ is the number of monolayers adsorbed on the surface, x is the ratio of partial pressure to equilibrium vapor pressure of the gas, and c is the ratio of partition function for a molecule in the first adsorbed monolayer to a molecule in the bulk liquid. c is an empirical constant to be determined.

To apply the B.E.T. model to the thickness, t, reported by a commercial monitor, the equation is $$t = D\theta + E \quad \text{(Eq.2)}$$

where D is a monolayer thickness and E is a constant to allow for an arbitrary initial thickness on the crystal.

The frequency, f, of the QCR is related to the thickness, t, by $1/f - 1/f_0 = K \, t/\rho$
where $f_0$ is the frequency of the crystal with no material absorbed, ρ is the density of the material absorbed, and K is a constant characteristic of the crystal vibration.

The parameter x in Eq. 1 is ratio of the partial pressure to the vapor pressure of the gas. For an ideal gas the partial pressure is the mole fraction, y, times the total pressure P. The vapor pressure for many gases can be accurately expressed by $$p^0 = A \, e^{-B/T} \quad \text{(Eq.3)}$$

so that $$x = yP/A \, e^{-B/T} \quad \text{(Eq. 4)}$$

where A and B are empirical constants, T is the absolute temperature. Equations 1, 2 and 4 can be used to relate the measured thickness, t, to the measured temperature, T. The five constants A, B, c, D and E can be adjusted to minimize the error between the measured data and the resulting model curve. Once the fitted coefficients are specified, the dewpoint, Tdp, can be calculated by setting Eq. 4 to unity resulting in $$T_{dp} = B/(ln(A) - ln(yP)) \quad \text{(Eq. 5)}$$

This system will cool the crystal at a sufficiently slow rate to ensure equilibrium conditions and calculate the best-fit parameters in the B.E.T. model that are used to determine the dewpoint.

Figure 4:
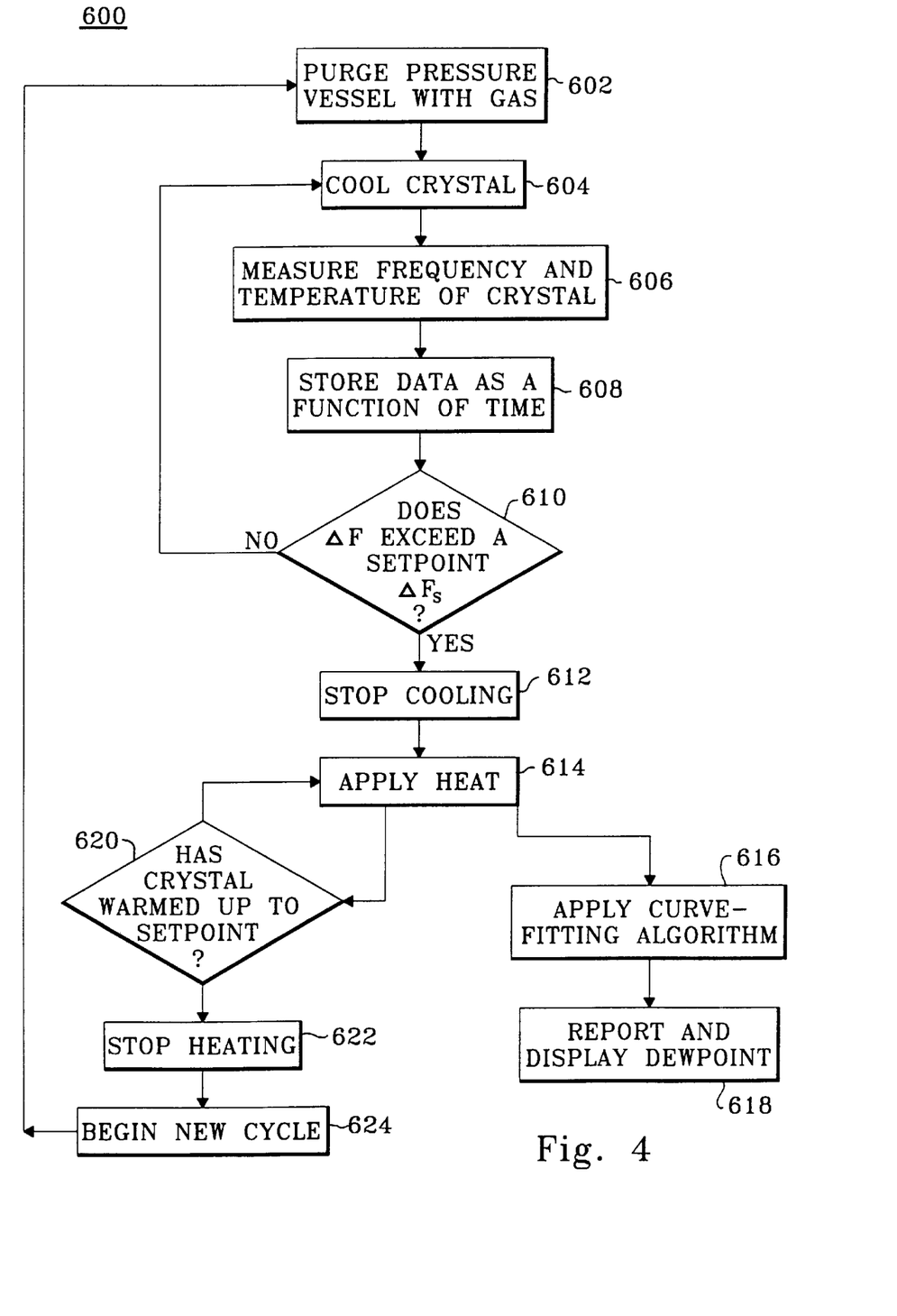
FIG. 4 is a flow chart depicting method steps in accordance with another embodiment of the instant invention.

A curve fitting method of determining gas quality using dewpoint sensor 100 is depicted in flow chart 600 of FIG. 4.

First, as shown in block 602, pressure vessel 104 is purged with a slipstream of gas flow 118 (FIG. 2). At block 604 (FIG. 4), circuitry 116 (FIG. 2) generates a signal to cooling device 122 to begin cooling QCR 112. Next, at block 606 (FIG. 4), circuitry 116 (FIG. 2) measures the frequency and temperature of QCR 112. The frequency and temperature measurements are then stored as a function of time at block 608 (FIG. 4).

At block 610, circuitry 116 (FIG. 2) monitors the frequency and temperature of QCR 112 to determine if the change in frequency ΔF over a predetermined period of time is greater than a set point change in frequency ΔFs. In this embodiment, ΔFs is selected to provide sufficient data to apply the curve fitting algorithm while maintaining the crystal above the dewpoint temperature. In one embodiment, ΔFs is in the range between about 1000 Hz to about 10,000 Hz and QCR 112 uses a 6 MHz crystal. If the value of ΔF does not exceed the value of ΔFs, the control sequence returns to block 604 (FIG. 4) and continues cooling QCR 112 (FIG. 2).

If, however, the value of ΔF exceeds the value of ΔFs, the temperature of QCR 112 is approaching the dewpoint of the gas flow. At block 612 (FIG. 4), the cooling is stopped. Heat is then applied to the crystal at block 614. Next, at block 616, the curve-fitting algorithm is applied to determine the dewpoint as discussed above. Because the dewpoint is calculated prior to cooling the crystal to the dewpoint temperature, the accumulation of liquids and particulates on the crystal is prevented.

At block 618, the calculated dewpoint temperature is reported, stored in a database or displayed to a system user.

At block 620, circuitry 116 (FIG. 2) monitors the temperature of the crystal to determine if the crystal has warmed up to a setpoint temperature. If the temperature of the crystal does not exceed the setpoint temperature, the control sequence returns to block 614 (FIG. 4) and more heat is applied to the crystal.

If, however, the temperature of the crystal exceeds the setpoint temperature, the control sequence advances to block 622.

At block 622, circuitry 116 (FIG. 2) generates a signal to heating device 124 to stop heating. At block 624 (FIG. 4), the control sequence begins a new cycle and returns to block 602.

If the dewpoint temperature is above a setpoint indicating contamination, circuitry 116 may, for example, limit turbine engine 10 to low load operation. Additionally, if the dewpoint temperature rises above a setpoint temperature, circuitry 116 may initiate an algorithm monitor combustion system anomalies.

The dewpoint temperature is related to gas quality by the calculated fuel superheat. For example, some fuel specifications call for gas fuel to be superheated by 50° F. Superheat is calculated by subtracting the measured dewpoint from the pipeline gas temperature.

Superheat=Pipeline gas Temperature−Gas Dewpoint Temperature>=fuel specification.

The dewpoint temperature must be a predetermined value below the pipeline gas temperature for the fuel to meet the specification. In a gas turbine application, the turbine control unit would calculate the gas superheat temperature based on measurements of pipeline gas temperature and gas dewpoint temperature. The control system will take action if the superheat criteria is not met. The action to be taken is subject to the accuracy in the measurement and the risk posed by bad gas. One approach is to indicate poor gas quality (Superheat<50° F.) as an alarm and not as a trip.

Figure 5:
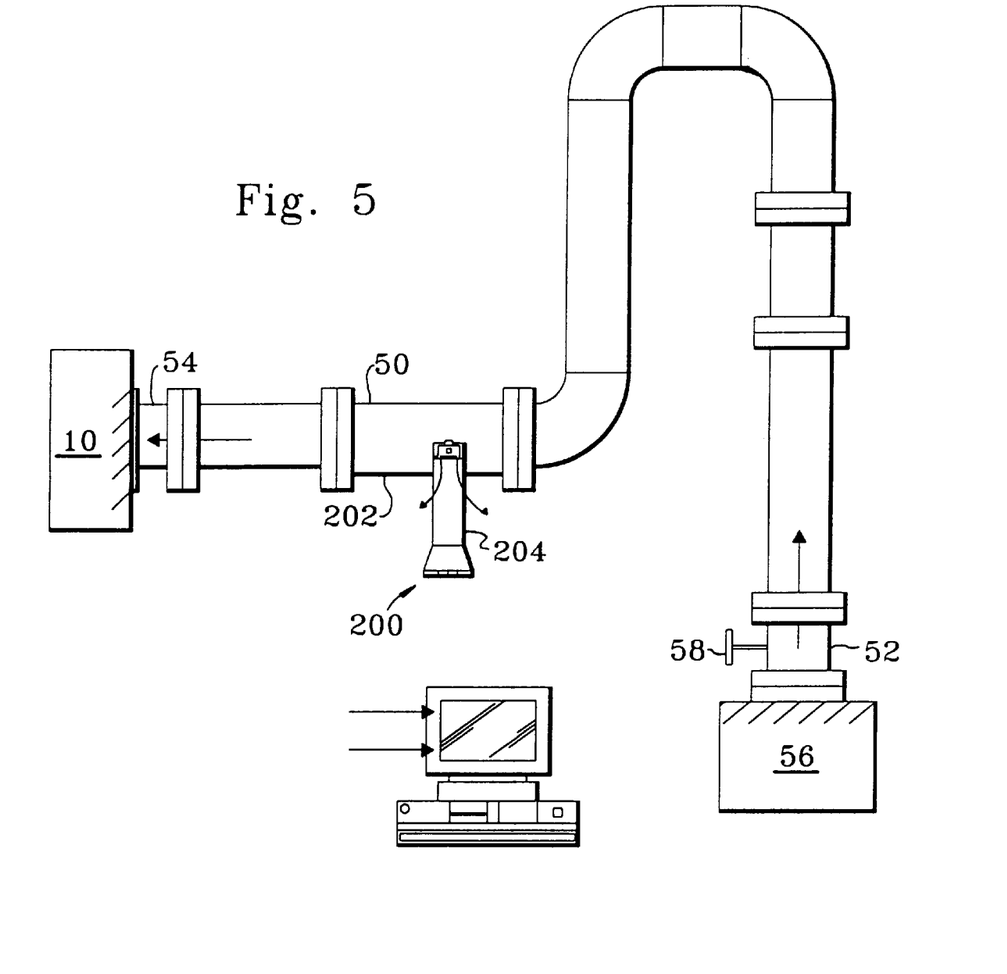
FIG. 5 is a schematic cross-sectional side elevation view of an inline dewpoint sensor in accordance with one embodiment of the instant invention.

In another exemplary embodiment of the instant invention, a pipeline 50 comprising an inlet 52 and an outlet 54 provides fluid communication between a fuel source 56 and power turbine 10, is shown in FIG. 5. A shut-off valve 58 is disposed within pipeline 50, which valve 58 is movable between a fully open position and a fully closed position to allow or prevent fuel flow, respectively, from fuel source 56 to power turbine 10.

In accordance with one embodiment of the instant invention, an inline dewpoint sensor 200 is disposed within a sidewall 202 of pipeline 50 for direct readings, as shown in FIG. 5.

Inline dewpoint sensor 200 comprises a housing 204 that is removably disposed within a sidewall 202 of pipeline 50. Housing 204 is disposed, with the appropriate seals (not shown) to prevent leakage of flow from pipeline 50.

Figure 6:
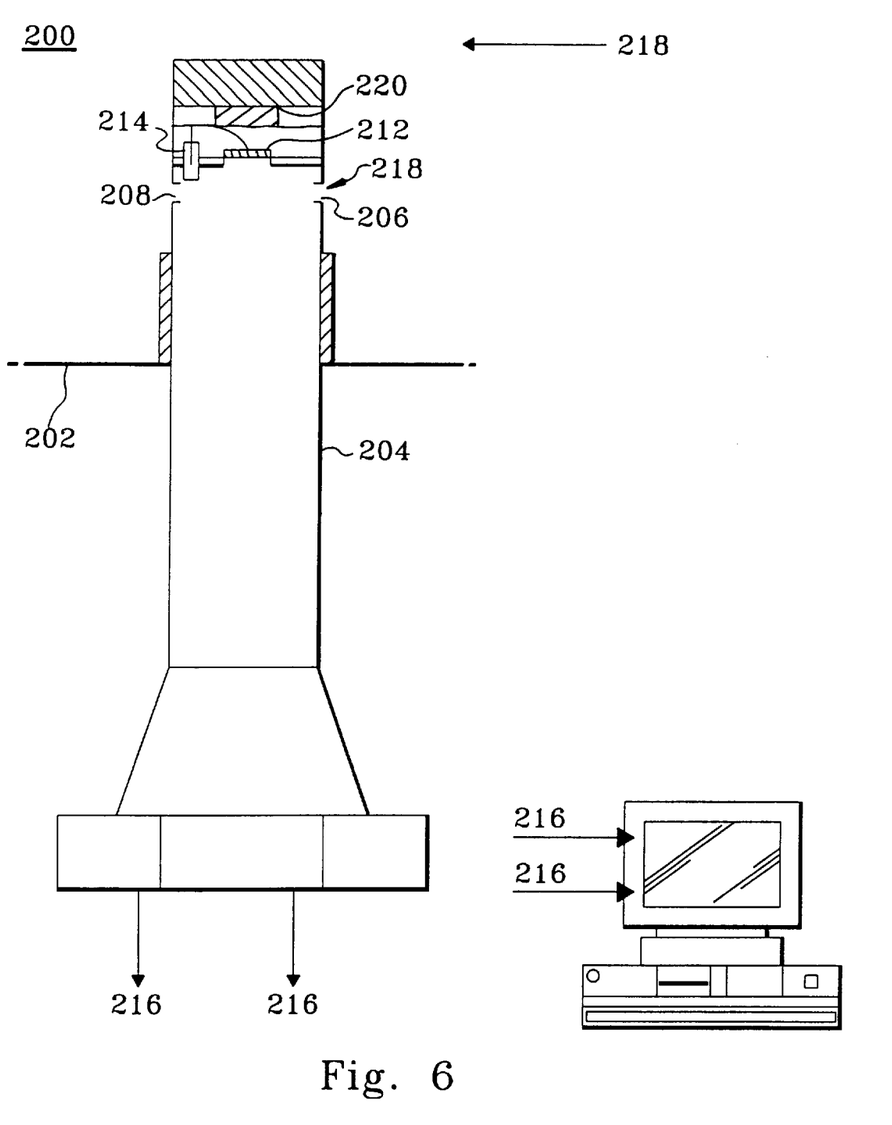
FIG. 6 is an enlarged schematic cross-sectional side elevation view of an inline dewpoint sensor in accordance with one embodiment of the instant invention.

Housing 204 comprises an entry port 206 and an exit port 208, as best shown in FIG. 6. A thermal connector 210 is disposed so as to extend within pipeline 50 through entry port 208. A quartz crystal resonator 212 is housed within housing 204 and is disposed in intimate contact with thermal connector 210. A temperature sensor 214 is disposed to generate signals representative of the temperature of quartz crystal resonator 212. Circuitry 216 is coupled to quartz crystal resonator 212 and temperature sensor 214. Circuitry 216 is configured to control the temperature of quartz crystal resonator 212, to measure the frequency of quartz crystal resonator 212, and to monitor the frequency of quartz crystal resonator 212 when exposed to a flow 218 between entry port 206 and exit port 208 so as to calculate a dewpoint value of fuel flow 218.

In one embodiment, circuitry 216 includes a power input and a processor for monitoring the signal and generating an output signal. In another embodiment, circuitry 216 comprises a computer 219 for processing signals and generating a dewpoint report and display.

Cooling of QCR 212 is typically by means of an internal cooler 220, for example, a thermoelectric cooler (TEC) with a heat sink or an external cooler, for example, a vortex tube or TEC. The connection of housing 204 to pipeline 50 can be via a pipe thread connection or other fastening means.

Methods for determining gas quality using dewpoint sensor 200 are depicted in flow charts 500 and 600, as previously discussed.

Figure 7:
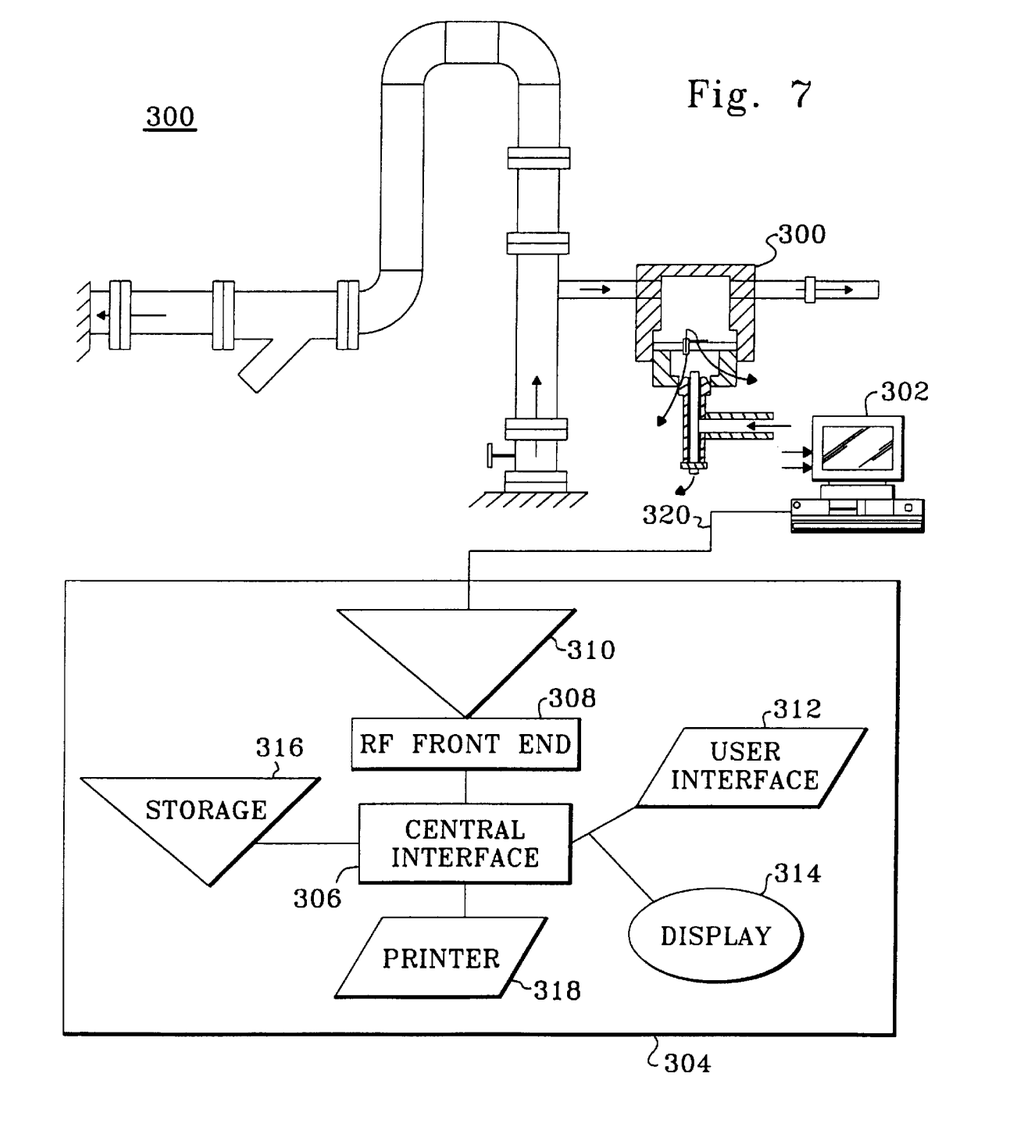
FIG. 7 is a schematic cross-sectional side elevation view of a remote dewpoint sensor in accordance with one embodiment of the instant invention.

A remote dewpoint sensor 300 is shown in FIG. 7. This embodiment is similar in all respects to the dewpoint sensor of FIG. 1 or FIG. 6, except that circuitry is electronically coupled to at least one remote unit 302 for transmitting signals from dewpoint sensor 300.

A remote station 304 provides a communication base for interaction with a respective remote unit 302. Remote station 304 typically comprises a central interface 306, a radio frequency (RF) front-end 308, an antenna 310 and user interface related peripheral devices including a user interface 312, a display 314, data storage 316 and a printer 318 for enabling a user to input relevant information into central interface 306. Peripheral devices as defined in this application include any device for storing dewpoint and of measurement or analysis information and intelligibly communicating the same to a system user, and include such devices as printers, hard disk drives, floppy disk drives, cathode ray tubes (CRTs) and keyboards. While only one set of respective peripheral devices are shown for a respective central interface 306, any number of peripheral devices may be utilized and are within the scope of the instant invention.

Methods for determining gas quality using dewpoint sensor 300 are depicted in flow charts 500 and 600, as previously discussed.

Communication between remote station 304 and a respective remote unit 302 is by way of a communication system 320, such as a "geo-synchronous" "L-band" satellite system, a "Little Leo" satellite system, a two-way paging system, a modem connection or any communication system capable of two-way communication between remote station 304 and a respective remote unit 302.

While only certain features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A dewpoint sensor comprising:
    a pressure vessel having an entry port, an exit port, and a temperature controlled plate;
    a quartz crystal resonator housed within said pressure vessel and disposed in intimate contact with said temperature controlled plate;
    a temperature sensor disposed to generate signals representative of said quartz crystal resonator temperature; and
    circuitry coupled to said quartz crystal resonator and said temperature sensor, which circuitry is configured to control the temperature of said quartz crystal resonator, to measure the frequency of said quartz crystal resonator and to monitor said frequency of said quartz crystal resonator as a function of time when exposed to a flow between said entry port and said exit port so as to calculate a dewpoint value of said flow,
    wherein said circuitry applies a curve-fitting algorithm to determine said dewpoint temperature of said flow without cooling said quartz crystal resonator to said dewpoint temperature to avoid accumulation of residue.

* * * * *